(12) United States Patent
Snyder et al.

(10) Patent No.: US 8,321,006 B1
(45) Date of Patent: Nov. 27, 2012

(54) BIOMETRIC DATA DISPLAY SYSTEM AND METHOD

(75) Inventors: Seth Snyder, Providence, RI (US); Jasper Speicher, Oakland, CA (US)

(73) Assignee: Humana Inc., Louisville, KY (US)

( * ) Notice: Subject to any disclaimer, the term of this patent is extended or adjusted under 35 U.S.C. 154(b) by 84 days.

(21) Appl. No.: 12/841,443

(22) Filed: Jul. 22, 2010

Related U.S. Application Data

(60) Provisional application No. 61/227,871, filed on Jul. 23, 2009.

(51) Int. Cl.
*A61B 5/044* (2006.01)
(52) U.S. Cl. ...................................................... 600/523
(58) Field of Classification Search .................. 600/513, 600/520, 522–525; 128/905, 920, 923
See application file for complete search history.

(56) References Cited

U.S. PATENT DOCUMENTS

| | | | |
|---|---|---|---|
| 2003/0181291 A1* | 9/2003 | Ogawa | 482/8 |
| 2004/0077934 A1* | 4/2004 | Massad | 600/300 |
| 2004/0171460 A1* | 9/2004 | Park | 482/8 |
| 2006/0040793 A1* | 2/2006 | Martens | 482/8 |

OTHER PUBLICATIONS

Electroplankton at Nintendo::Games, Game Overview, http://www.nintendo.com/games/detail/db2f8da6-2e1b-48cb-b142-a90899e8a1a8, Jan. 9, 2006.

* cited by examiner

*Primary Examiner* — George Evanisko
(74) *Attorney, Agent, or Firm* — Standley Law Group LLP

(57) ABSTRACT

An interactive biometric display system and method for collecting and displaying biometric data. The display system comprises a device for identifying a user and at least one biometric input device (e.g., heart rate sensor). A user provides identifying data via the identifying device and biometric data via the biometric input device. The biometric data (e.g., heartbeat) is measured and recorded with a timestamp. Graphical objects for each user are presented (e.g., a heart) and move around the screen in relation to the biometric data. Attributes of graphical objects (e.g., size, color, color saturation, and height) may vary over time indicating the recency of the data. The display system may further comprise a sound component to play sound related to the biometric data. Visual as well as sound attributes may diminish, fade, or disappear over time and may be refreshed when a new reading for the user is received.

20 Claims, 11 Drawing Sheets

BIOMETRIC DATA DISPLAY SYSTEM AND METHOD

CROSS-REFERENCE TO RELATED APPLICATIONS

This application claims priority to U.S. Provisional Application Ser. No. 61/227,871, filed Jul. 23, 2009, titled SYSTEM AND METHOD FOR DISPLAYING BIOMETRIC DATA, the content of which is incorporated by reference as if fully recited herein.

FIELD OF THE INVENTION

The present invention relates to computerized systems and methods for encouraging users to increase awareness and concern for their health and wellness through the collection and display of biometric data. In particular, the present invention relates to an interactive display system and method that provides visual and auditory representations of comparative biometric data (e.g., heart rates) of users in a visually attractive and rewarding manner.

BACKGROUND OF THE INVENTION

Obesity is increasing across many segments of society. Also increasing are the health complications that obesity causes, such as diabetes, heart disease, hypertension, and stroke. The most effective way to avoid obesity and its associated health complications is to live a healthy, active lifestyle, which includes regular exercise, healthy eating, and vigilantly monitoring one's overall well-being (such as taking readings for blood pressure, heart rate, etc.). Although it is relatively easy for individuals to determine if they are regularly exercising and eating properly, monitoring one's overall well-being is not quite as simple. Most individuals do not have the proper devices or equipment to monitor vital signs and other biometrics. Furthermore, they may not understand the data produced by the devices or equipment. Finally, even if they have the proper devices or equipment, they may not be motivated to use it. Use of the devices or equipment simply is not fun or entertaining.

Awareness of one's overall well-being is a vital part of a healthy lifestyle. Evidence suggests that employees can benefit greatly from an increased awareness and concern for their health and wellness as recent studies show a correlation between job-induced stress and unwanted weight gain, as well as working overtime and heart health. Employees are not the only ones that benefit from the increased awareness. Employers also benefit from initiatives to increase employee awareness of their well-being by realizing a reduction in costs related to healthcare and lost productivity.

Consistently monitoring one's vital signs or biometrics is an effective way for individuals to increase awareness of their health and wellness. Nonetheless, individuals typically do not check their biometrics often enough because the experience of doing so is not convenient, rewarding, or stimulating nor does it confer an immediate benefit. For many individuals, monitoring physical activity, such as through the use of a pedometer, is convenient and rewarding in that the device provides feedback using simple and easy-to-comprehend visual representations. For many individuals, monitoring devices such as pedometers confer immediate gratification to users, and therefore, they are more likely to continue using them.

Even with devices that monitor physical activity, motivation to continue the activity can diminish or cease over time. Thus, it is important to have a continuous source of inspiration for individuals to keep them involved in monitoring their well-being. It is especially important to provide, whenever possible, an element of fun in the activity because people are more likely to be proactive when they perceive an activity as being fun and not simply another chore or task. Friendly competition is another element of fun that can inspire people to habitually check their biometrics. Because many people enjoy visual and auditory presentations, incorporating graphical representations and music or sounds in an interactive display of data can make the activity even more enjoyable and increase motivation to monitor their biometrics.

Therefore, there is a need for a system and method for collecting and displaying individuals' biometric data in a convenient and artistic manner. There is also a need for a system and method that allows individuals to compare their biometric data with the biometric data of their peers. There is also a need for a fun and entertaining way of visually representing the most recently collected biometric data of multiple individuals and updating the representation to illustrate, for example, how many times an individual has scanned their biometric data that day.

SUMMARY OF THE INVENTION

The present invention is an interactive biometric display system and method for collecting and displaying biometric data. In an example embodiment, the biometric data is heart rate data. The animated, biometric display and equipment may be installed in an office or other facility, preferably in a location that is easily accessible to the individuals that enter or use the facility. In an example embodiment, the display system comprises a device for identifying a user such as an RFID reader. The display system further comprises at least one biometric input device. In an example embodiment, hand grip heart rate sensors are used to measure each user's heart rate. When a user grips the handles of the heart rate sensor, his or her heartbeat is measured and recorded.

The time of the measurement is also recorded. The display system may further have audio output functionality and at least one speaker to play audible signals in connection with biometric data. A graphical object for each user that provides data is presented on the display. In addition, a musical layer to an electronic orchestral piece is added for each user. Visual attributes of the graphical objects as well as attributes of the music are displayed and varied according to the user's heartbeat data as well as the recency of the data.

Graphical objects for each user move around on the screen, pulsing and bouncing off the walls of the screen. The speed or rate of movement may diminish over time to indicate that the user has not recently interacted with the display system. Other attributes of the graphical object may be varied over time as well such as size, color, color saturation, and height on the screen. Attributes of the musical display may also vary over time. Each user's musical layer may diminish or disappear over a specified period of time. Attributes that diminish, fade, or disappear over time may be refreshed or intensified when a new reading for the user is received at the display system.

DETAILED DESCRIPTION

The present invention is an interactive biometric display system and method for collecting and displaying biometric data. In an example embodiment, the biometric data is heart rate data and the biometric input device is a hand grip heart sensor. Other types of sensors such as ear clip pulse sensors or finger pulse sensors could be used. Examples of other biometric data that could be collected and displayed include: blood pressure, respiratory rate, and temperature. Data from any physiological function that can be measured may be used in connection with the biometric display system and method. The animated, biometric display and equipment may be installed in an office or other facility, preferably in a location that is easily accessible to the individuals that enter or use the facility.

Figure 1A:
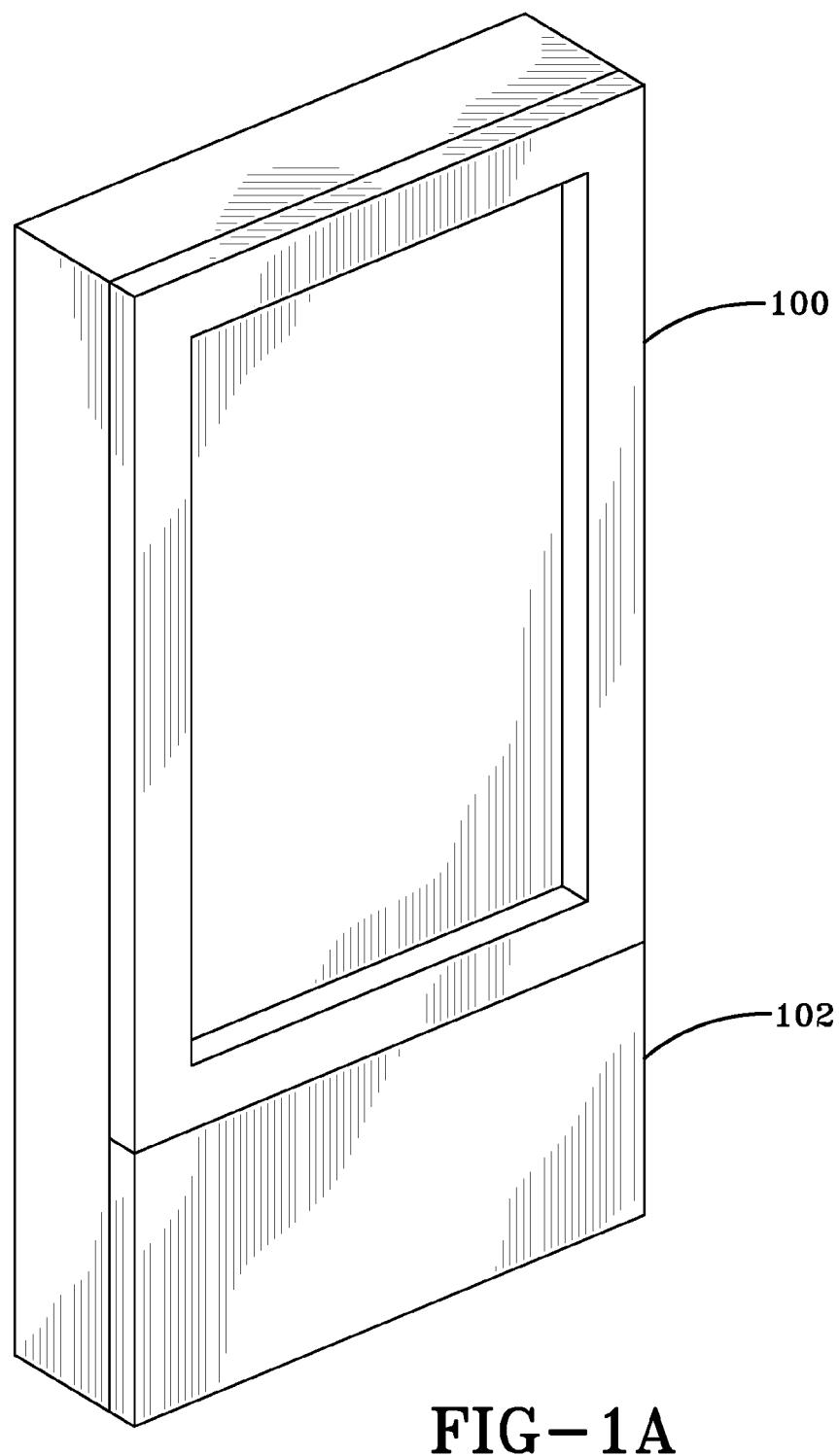
FIGS. 1A-1C are perspective views of a cabinet comprising components for a biometric data display system according to an example embodiment.
Figure 1B:
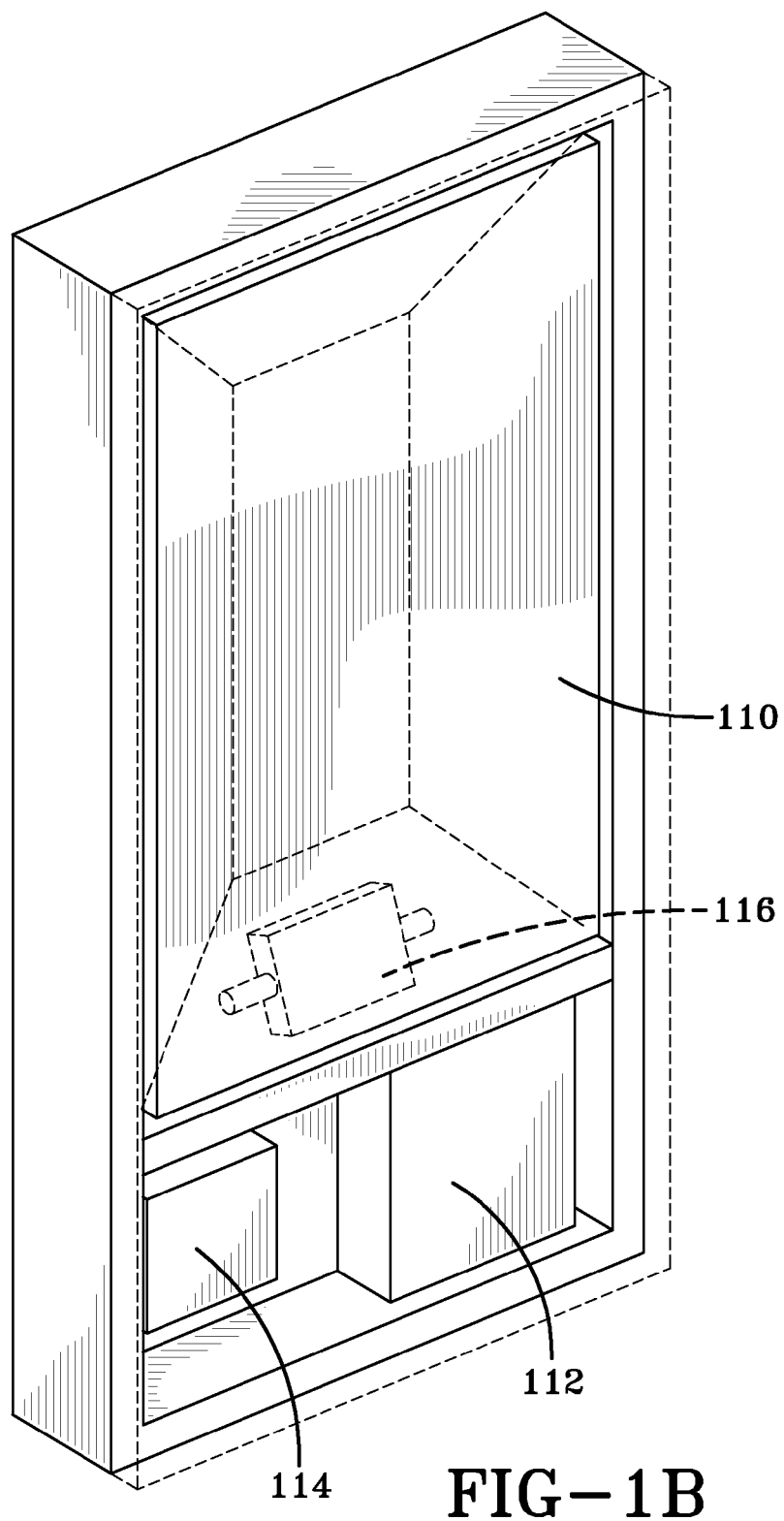
Figure 1C:
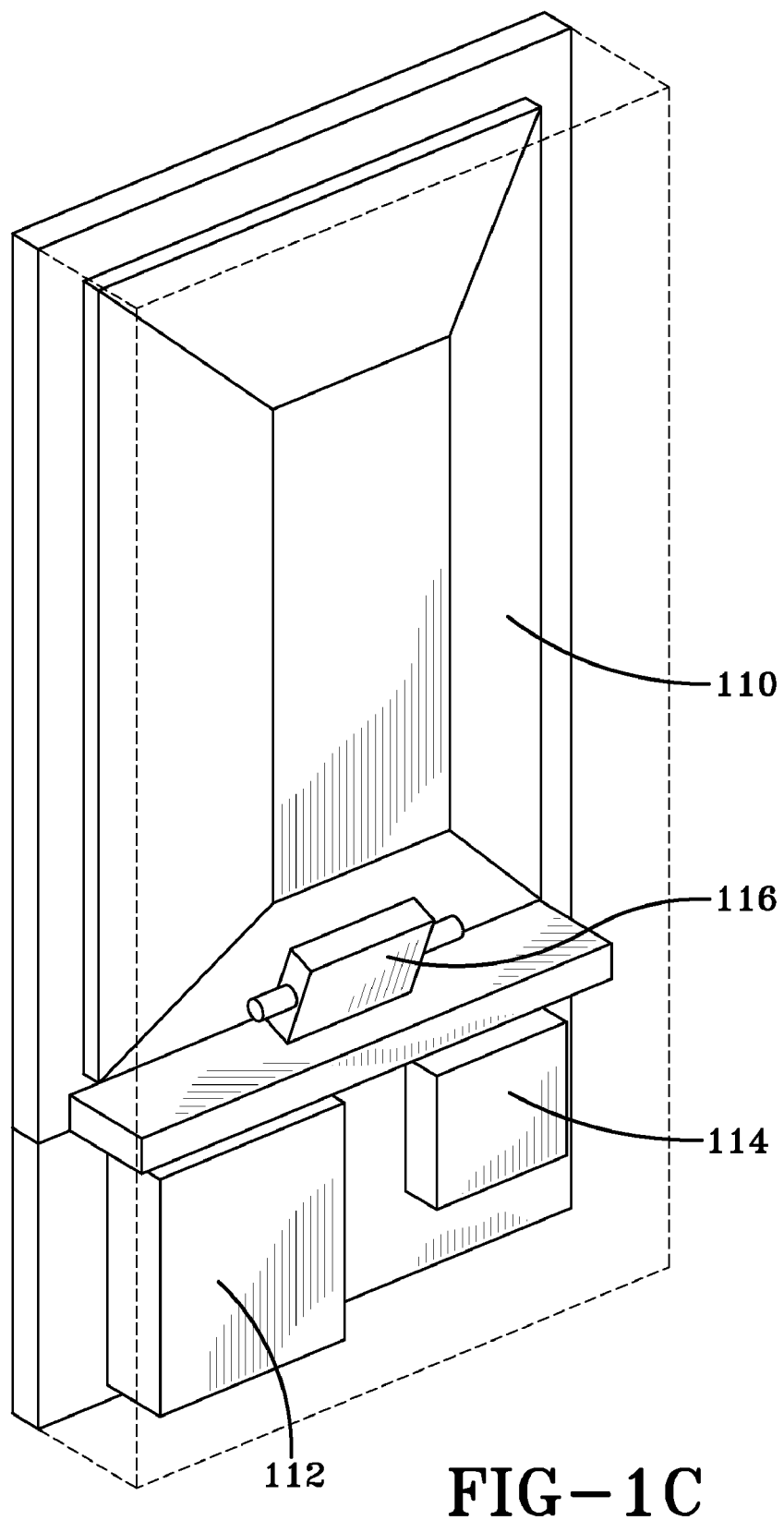

Referring to FIGS. 1A-1C, perspective views of a cabinet comprising components for a biometric data display system according to an example embodiment are shown. FIG. 1A is a perspective view of a cabinet and display. A display screen may be housed in an upper portion of the cabinet 100 while a computer and other components and equipment to drive the display screen are housed in a lower portion 102. FIG. 1B is a frontal transparent perspective view of the cabinet to illustrate the location of certain components within the cabinet. The display system comprises a computer or processor 112 for receiving user identifying data and user biometric data. It further comprises a computer monitor or display screen 110, one or more speakers, an RFID reader 116, a transceiver 114 that communicates with the biometric data device and the computer, a ventilation fan, and a power strip. FIG. 1C is a posterior transparent view of the cabinet to illustrate the location of various components within the cabinet.

The processor executes a software application for receiving user input (identifying data and biometric) data and entering it in a log file with a timestamp. The software application also generates and displays on a screen a graphical object for each user that provides input data. Attributes of the graphical object reflect the user's biometric data. The graphical objects may be animated and move around the screen to provide feedback regarding the data that has been collected as well as to attract new users. Current users may also be drawn to the display to update their data.

In an example embodiment, the display system comprises an RFID reader so that users may identify themselves to the computerized system. In alternative embodiments, barcode scanners or magnetic card readers may be used to receive identifying information from users or a conventional keyboard and/or mouse may be provided to allow users to login to the computerized system. Additionally, the display system comprises biometric input devices. Various devices to record biometric data may be used. In an example embodiment, hand grip heart rate sensors are used to measure each user's heart rate. When a user grips the handles of the heart rate sensor, his or her heartbeat is measured and recorded. The time of the measurement is also recorded. In example embodiments of the invention, the display system is further equipped with audio output functionality and at least one speaker to play audible signals in connection with biometric data. For example, the audible signals may be orchestral music played in "layers," each of which is assigned to a user of the display system. As users interact with the system, additional musical layers are added and played.

Figure 2:
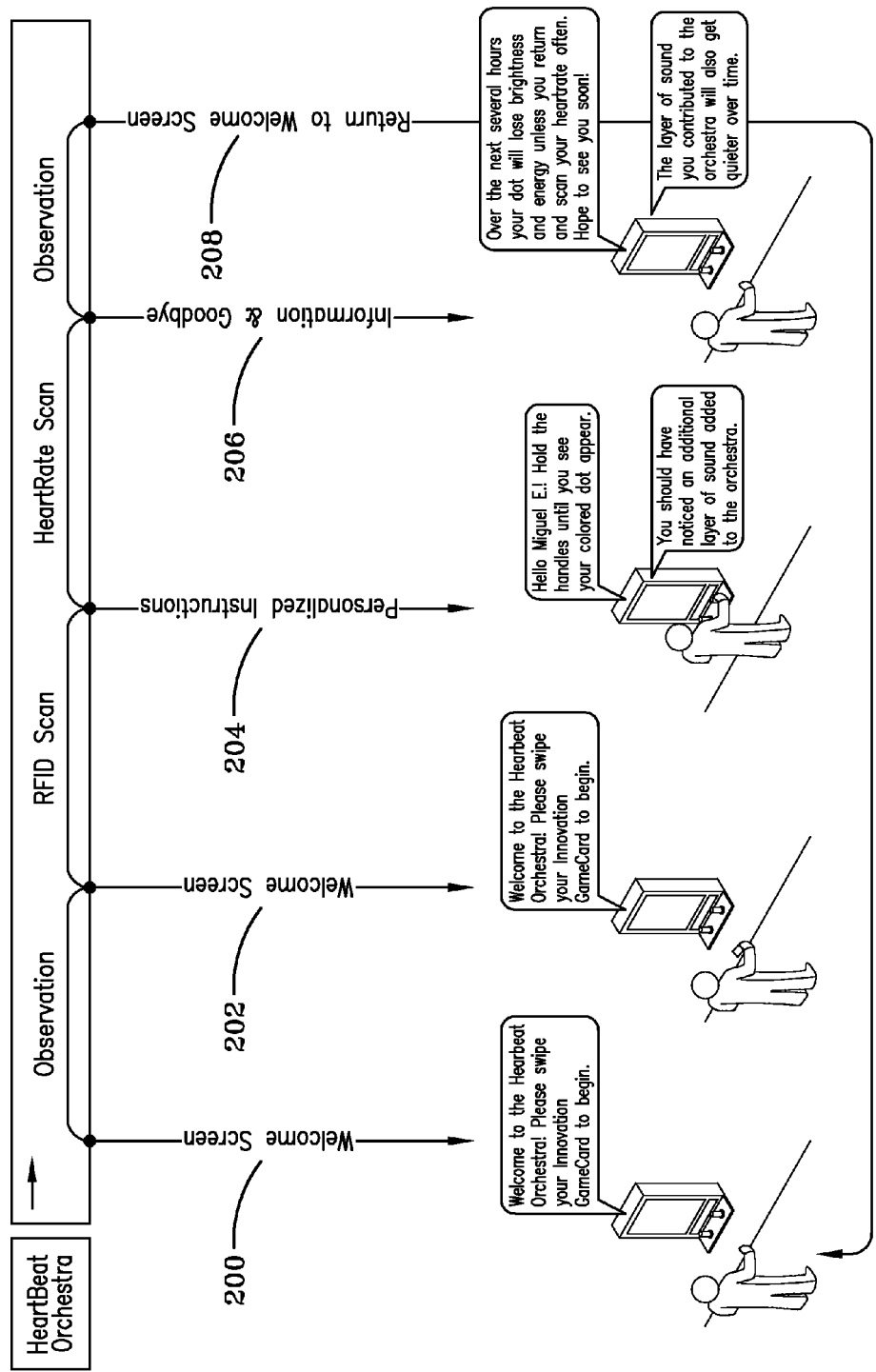
FIG. 2 is a flow diagram illustrating use of the biometric display system according to an example embodiment.

Referring to FIG. 2, a flow diagram illustrating use of the biometric display system according to an example embodiment is shown. Initially, a welcome screen is displayed to a user that approaches the display system 200. The user is prompted to provide identifying information to the system 202. In an example embodiment, users are provided with RFID cards to communicate with the display system. Users scan their RFID cards to enter the interface 202. In an example embodiment in which user heart rates are measured using hand grips, the user is then instructed to place his or her hand on a heart rate sensor handle 204. Upon receiving the heart rate data, the computerized system generates and displays a graphical object labeled with the user's name. The graphical object then pulses to the beat of the user's heart.

In an example embodiment in which the display system further comprises audio functionality, the system may further play sounds in addition to presenting a graphical object. In an example embodiment, the audio functionality is an orchestral electronic musical piece comprising "layers." A new layer is added for each new user that interacts with the system. The sound produced, therefore, may be a dynamically changing layered electronic piece. The graphical objects and musical layers are representative of the heartbeat data that has been collected from the plurality of users.

Depending upon the number of times that a user provides heart rate data during the day (or another time period), his or her graphical object on the display varies in appearance. Initially, a user's graphical object moves around on the screen, pulsing and bouncing off the walls of the screen to indicate an "energy level." In an example embodiment, the "energy level" of the graphical object diminishes over time to indicate that the user has not recently interacted with the display system. Other attributes of the graphical object may be varied over time as well such as size, color, color saturation, and height on the screen. In an example embodiment, the user is informed that his or her graphical object will lose brightness and energy and the musical layer contributed to the "orchestra" will diminish unless the user updates his or her heart rate data 206. After the user provides his or her biometric data, the welcome screen on the display returns 208 so that the next user may interact with the display system.

Each time a user re-visits the display system to provide heart rate data, his or her graphical object reflects the new scan by changing its visual and/or aural characteristics. In an example embodiment, the user's graphical object is "re-energized" so it moves faster and the user's sound layer increases in volume. One of skill in the art would understand that the specifics of the visual and/or aural attributes and animation may be refined in a variety of ways.

Figure 3A:
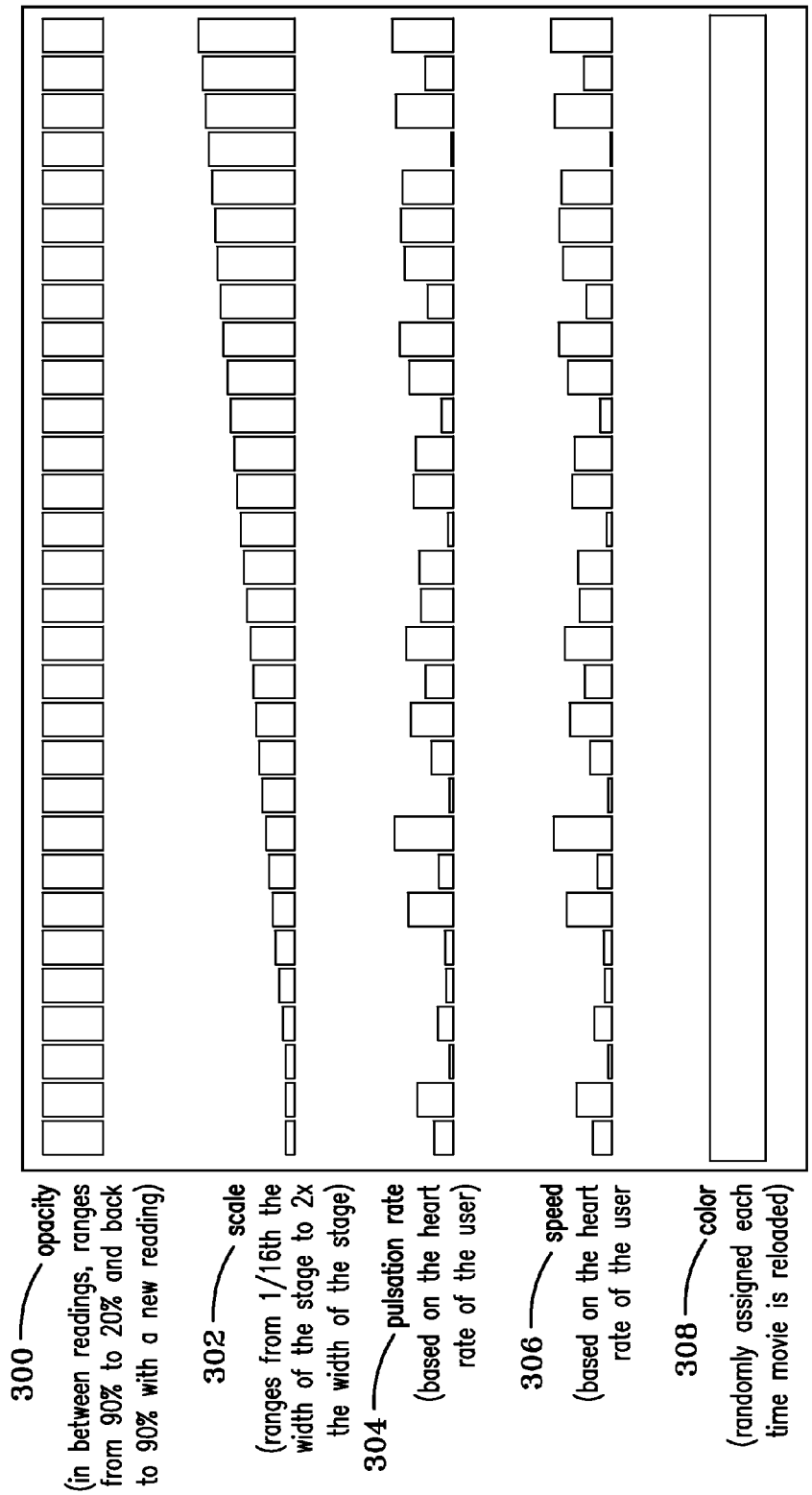
FIGS. 3A and 3B are diagrams illustrating object attribute variations according to an example embodiment.
Figure 3B:
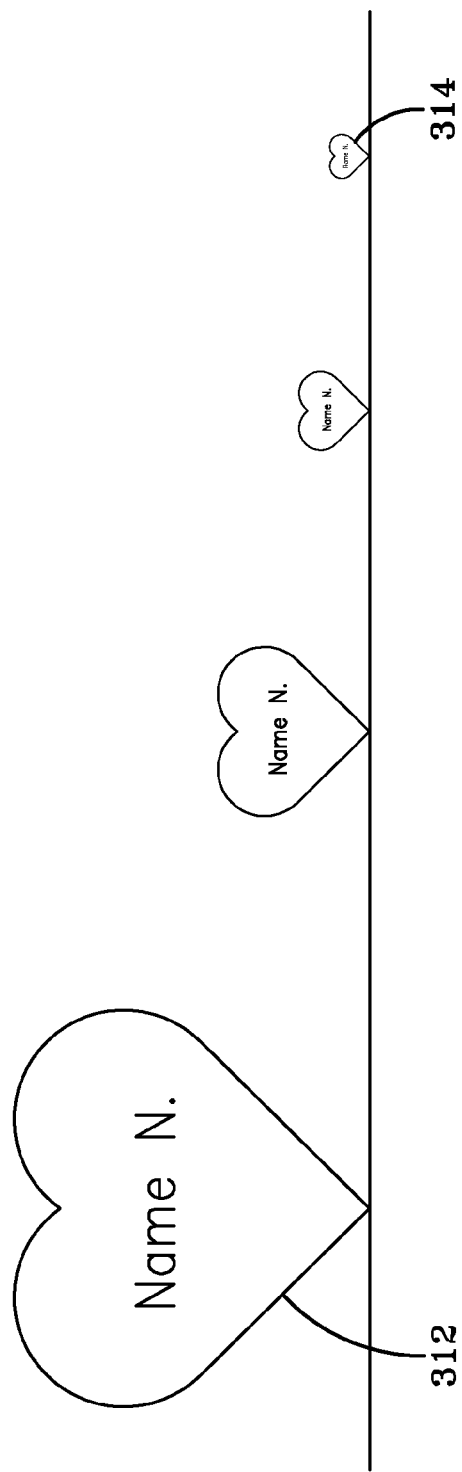

Referring to FIGS. 3A and 3B, diagrams illustrating object attribute variations are shown. As indicated in FIG. 3A, visual attributes such as object opacity 300, object scale 302, pulsation rate 304, object speed 306, and object color 308 may be varied. In an example embodiment, a "maximum per day" parameter 310 may be established to limit the visual effect changes during the day or other applicable time period. Referring to FIG. 3B, an illustration of object scale variations is shown. As indicated in the illustration, four sizes of the same graphical object may used to reflect the value and/or recency of user heartbeat data. The graphical object of a user that has just provided biometric data may be rendered in the largest size 312 while the graphical object of a user that has the oldest data may be rendered in the smallest size 314. Each scan of a user's heartbeat may cause the graphical object to return to its largest size as well as to change color and color saturation. In addition the scan may cause the volume of the user's musical layer to increase. Attributes may intensify with refreshed data.

Figure 4A:
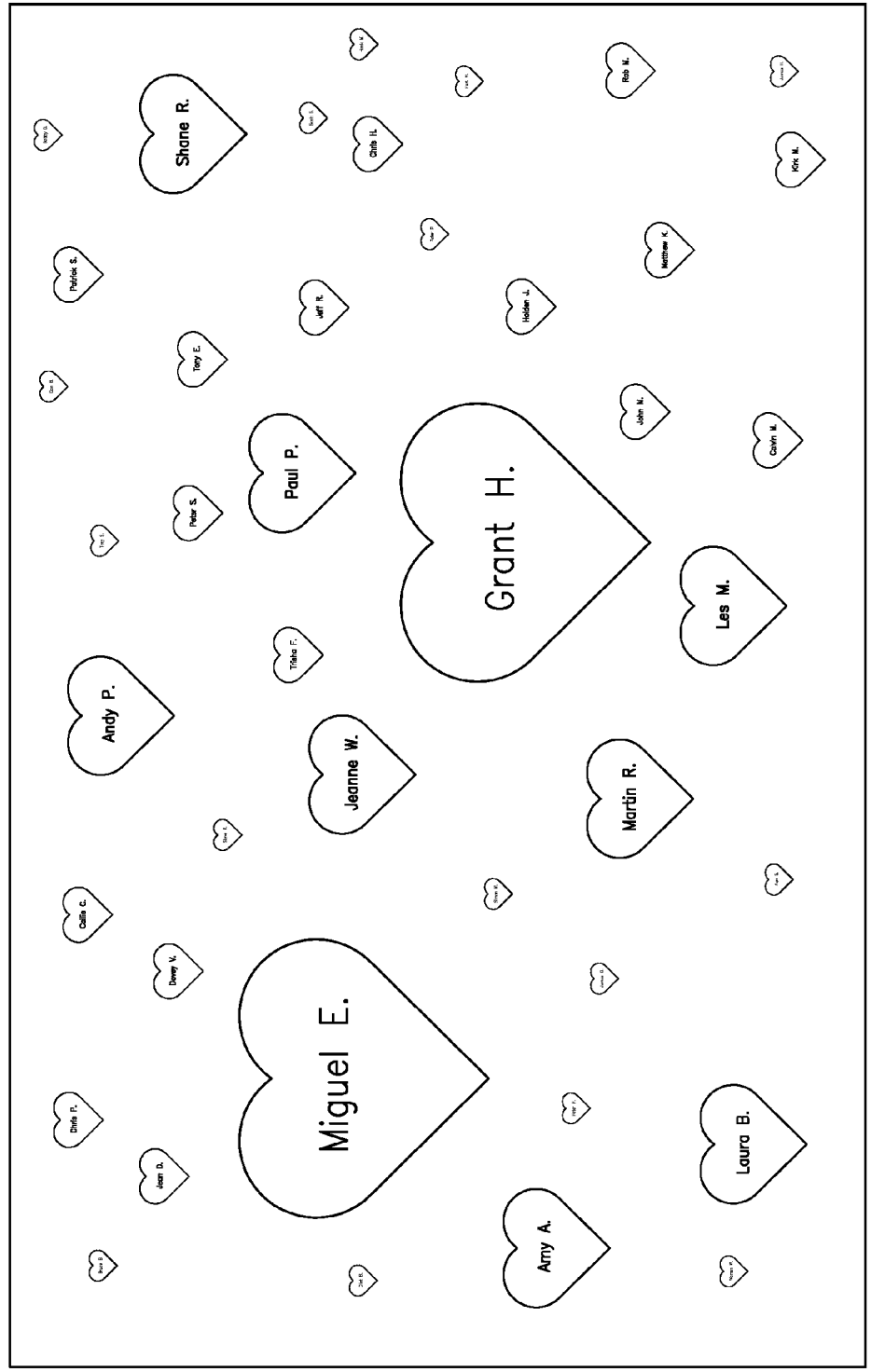
FIGS. 4A and 4B are example displays comprising graphical objects associated with biometric data according to an example embodiment.
Figure 4B:
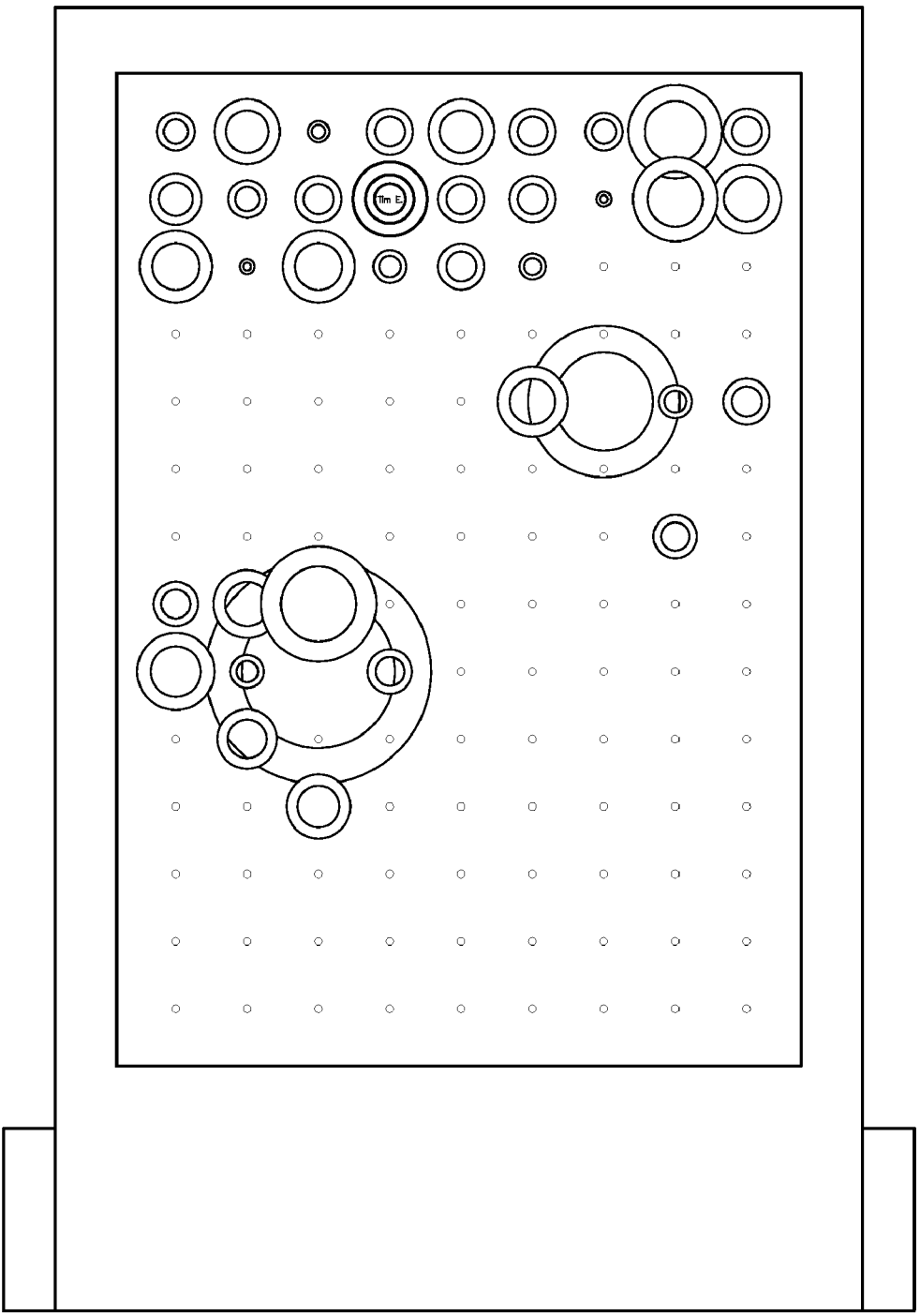
Figure 4D:
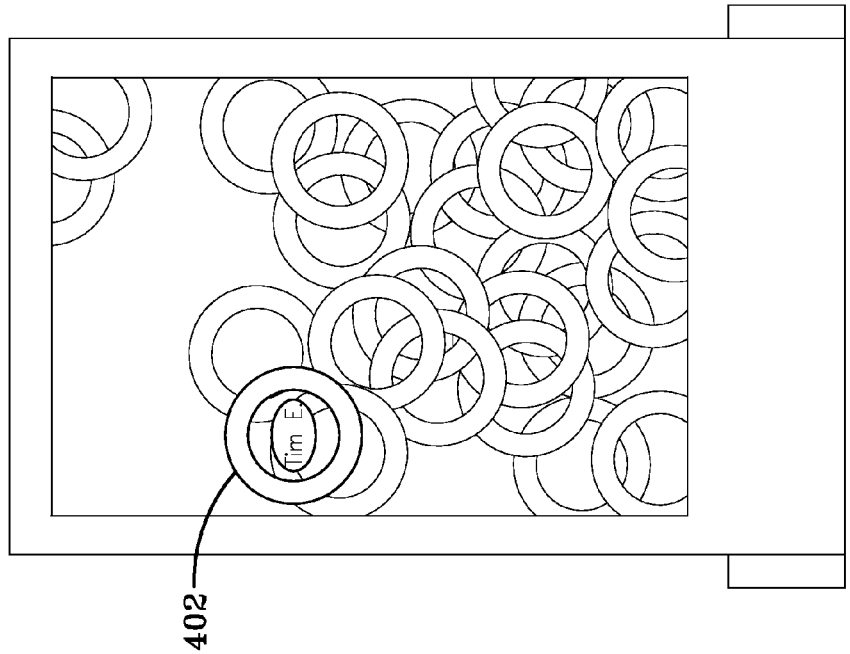
FIGS. 4C-4H illustrate the movement and variations in appearance of graphical objects according to an example embodiment
Figure 4C:
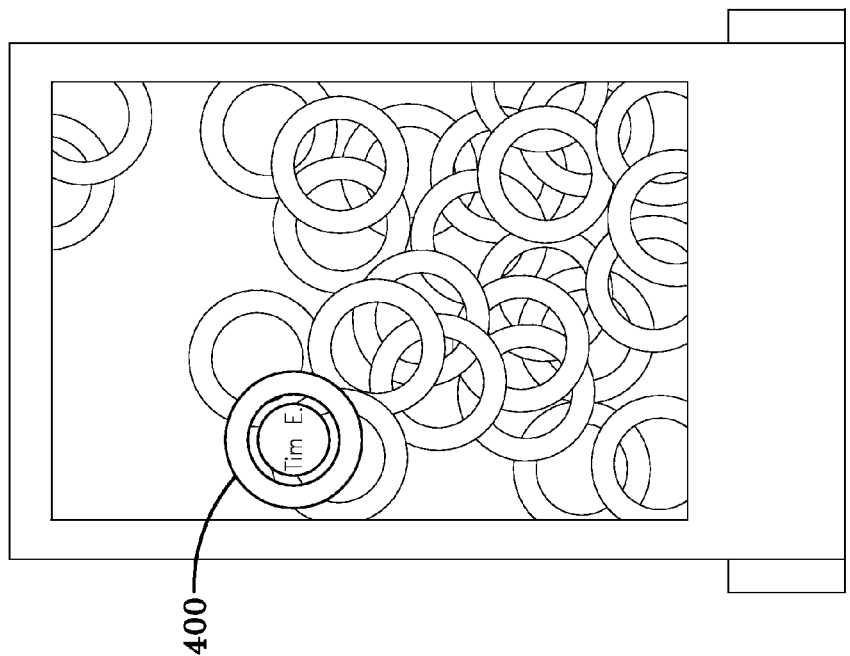
Figure 4F:
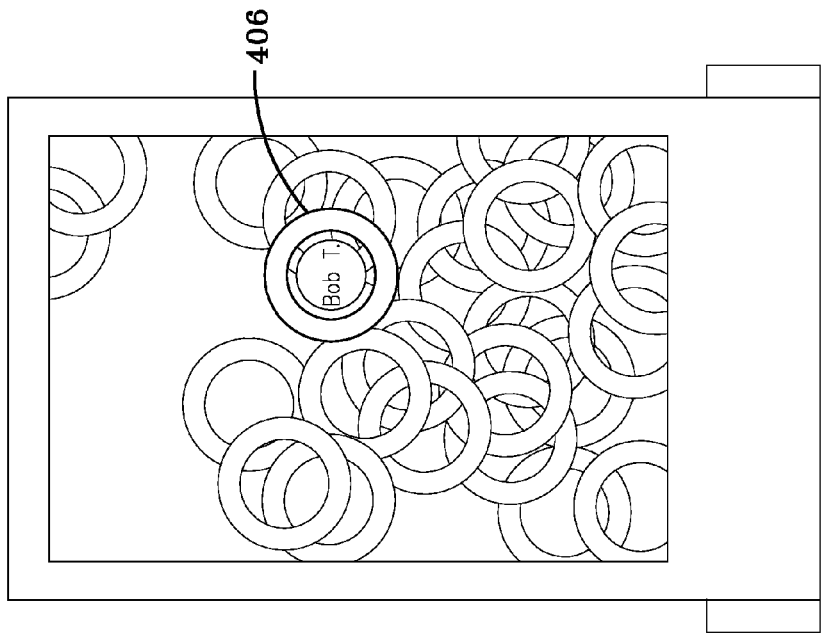
Figure 4E:
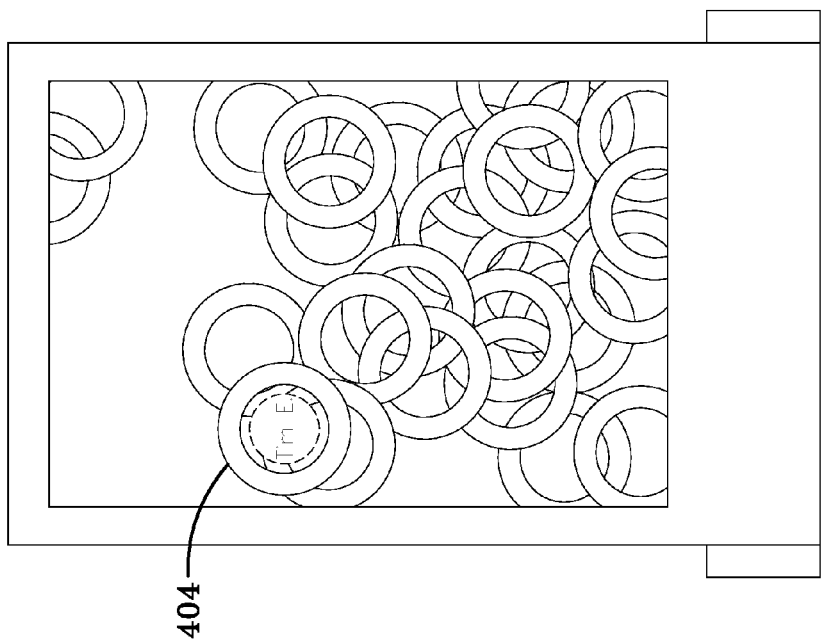

Referring to FIGS. 4A and 4B, example displays comprising graphical objects associated with biometric data according to an example embodiment are shown. As indicated in FIG. 4A, the user's name or other identifying information appears in a graphical object such as a heart. Various attributes of the graphical object such as the size and placement on the screen may reflect the value of the user's biometric data as well as the recency of the user's biometric data. The object may "pulse" in relation to the value of the user's heartbeat. As explained previously, the objects may also move or bounce around the screen in relation to an "energy level" related to the recency of the data. The objects of users with the most current data may have higher energy levels than the objects of users with older data. The timestamp data is used to determine the recency of each user's data.

FIG. 4B illustrates the use of graphical objects in the form of concentric circles or rings. As with the heart-shaped objects, the user's name appears in the center. As with the heart-shaped objects, the ring objects may pulse according to the user's own pulse data and move according to an energy level. The size, placement, and other attributes of the objects may vary according to the level of the heartbeat data as well as the recency of the heartbeat data. As FIGS. 4A and 4B illustrate, the display system reflects the number of times every user in the facility has provided his or her heart rate data that day (or during another time period). Each user's input affects characteristics of the display and therefore, may be inspired to frequently provide data. Each user has the ability to boost his or her object's visual prominence on the display as well as auditory influence on the "orchestra."

Figure 4H:
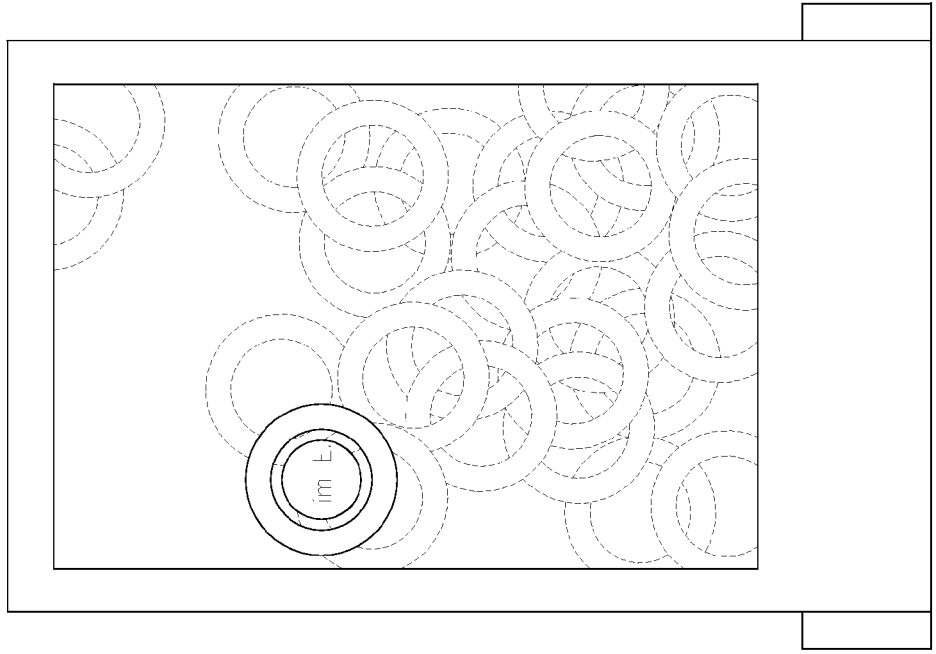
Figure 4G:
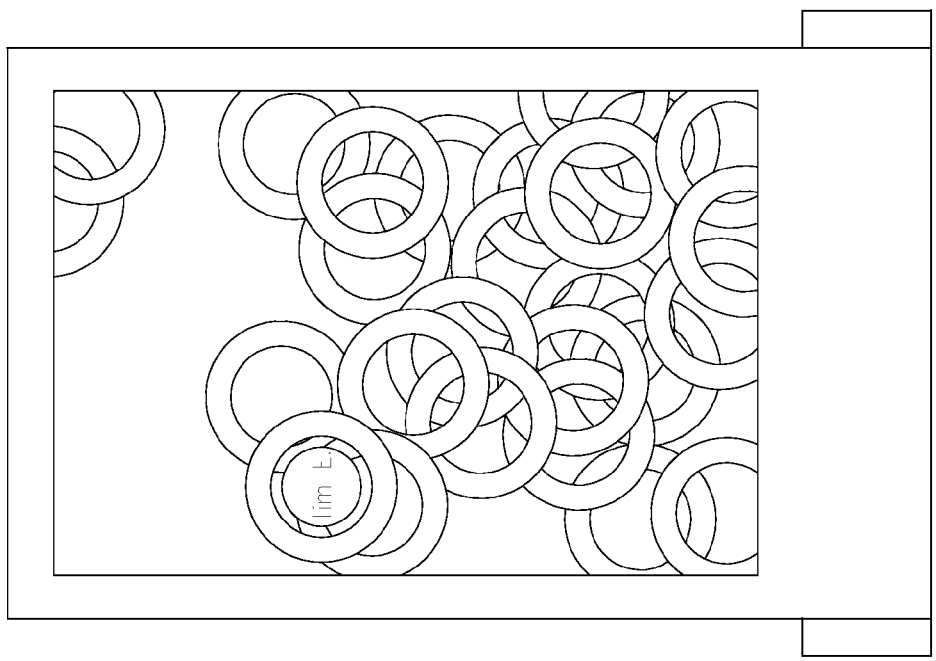

FIGS. 4C-4H illustrate the movement and variations in appearance of graphical objects according to an example embodiment. In the example shown, a plurality of rings move around the screen. When a user swipes an RFID card at the display station, the user's name appears in the associated object (e.g., ring) 400. In the example shown, the user's name appears inside a circle within the ring. Animation software in the display system causes the inside circle to shrink and expand (i.e., pulse) 402 according the user's heartbeat data. For embodiments comprising audio output, the level of sound may also correspond to the heartbeat data. After a period of time (e.g., seconds or minutes), the inside circle fades and disappears from the display 404. When another person approaches the display system, the user's name appears in an associated object 406 and shrinks and expands (i.e., pulses) according to the heartbeat data. In an example embodiment, a user's object may blur or fade over time if the user's data is not refreshed. FIGS. 4G and 4H illustrate an example change in the appearance of the display over time. Rings with sharply defined edges appear in FIG. 4G while rings with blurred edges appear in FIG. 4H. If no new data is received within a certain time period, all of the objects appearing in the display may have blurred edges. When new data is received, the ring edges of the users providing refreshed data may be sharpened. Various attributes may be revived or intensified as new user data is received.

In an example embodiment, the heart rate sensor data is associated with Adobe Flash® code that causes objects to move and bounce around on a display screen based on the user's heart rate and/or frequency of readings. In an example embodiment comprising an audio output component, music is presented as a multi-layered, looping sound scape. Each object on the screen has a layer of sound scape associated with it, and each object is associated with a user's RFID card. A log file is generated with time-stamped user identifiers and heart-rate data.

The sound is constructed layer-by-layer with each new person that provides heartbeat data. The number of layers that are used as well as fade time for layers may be varied. In an example embodiment in which 10 layers of sound are deployed and each sound layer fades after a minute, the display system may operate as follows. If ten individuals approach the display system and provide data back-to-back over the course of ten minutes, each sound layer is deployed and the "orchestra" plays to its full capacity. After the eleventh minute, the sound returns to nine layers. After the twelfth minute, the sound returns to eight layers, and so on. Eventually, the sound returns to a single layer until another user provides input. In an example embodiment, layers may also be varied according to the location of the objects on the screen.

While certain embodiments of the present invention are described in detail above, the scope of the invention is not to be considered limited by such disclosure, and modifications are possible without departing from the spirit of the invention as evidenced by the claims. For example, user identification and biometric input devices may vary and fall within the scope of the claimed invention. The types of graphical or visual objects as well as their attributes may be varied and fall within the scope of the claimed invention. Other aspects of the system and display characteristics may be varied and fall within the scope of the claimed invention. One skilled in the art would recognize that such modifications are possible without departing from the scope of the claimed invention.

The invention claimed is:

1. A biometric data display system comprising:
    (a) a user identification device;
    (b) a biometric data input device;
    (c) a screen display; and
    (d) a processor programmed for:
        (1) receiving from a plurality of users user identification data from said user identification device;
        (2) receiving from said plurality of users user biometric data from said biometric input device and a timestamp for said biometric data;
        (3) generating a plurality of graphical objects wherein each object is associated with a user's identification data, said timestamp for said biometric data, and an attribute representative of said biometric data;
        (4) presenting said graphical objects on said screen display;
        (5) animating each of said graphical objects on said screen display in relation to said attribute for said object; and
        (6) periodically reviewing said timestamp for each of said graphical objects to identify at least an oldest timestamp;
        (7) updating said screen display to diminish an attribute of a graphical object associated with said oldest timestamp.

2. The system of claim 1 further comprising a speaker for providing audio output in relation to said animation attribute.

3. The system of claim 1 wherein animating each of said graphical objects on said screen display in relation to associated user biometric data comprises varying over a period of time said attribute of each of said graphical objects.

4. The system of claim 3 wherein said attribute of said graphical object is selected from the group consisting of:

speed, size, color, color saturation, and height on the screen.

5. The system of claim 3 wherein said time period is a day.

6. The system of claim 3 wherein said time period is a period of minutes.

7. The system of claim 3 wherein said attribute intensifies when new biometric data is received.

8. The system of claim 3 wherein said attribute of said graphical object is a location of said graphical object on said screen display.

9. The system of claim 1 wherein said biometric input device is a heart rate sensor.

10. The system of claim 9 wherein said heart rate sensor is selected from the group consisting of:

hand grip sensors, ear clip sensors, and finger sensors.

11. A computerized biometric data display method comprising:
    (a) receiving at a computer from a plurality of users user identification data;
    (b) receiving at said computer from said plurality of users user biometric data and a timestamp for said biometric data;
    (c) generating at said computer a plurality of graphical objects wherein each object is associated with a user's identification data, said timestamp for said biometric data, and an attribute representative of said user biometric data;
    (d) presenting on a screen display for said computer said graphical objects; and
    (e) animating on said screen display each of said graphical objects in relation to said attribute for said object;
    (f) periodically reviewing said timestamp for each of said graphical objects to identify at least an oldest timestamp;
    (g) updating said screen display to diminish an attribute of a graphical object associated with said oldest timestamp.

12. The method of claim 11 further comprising providing through a speaker audio output in relation to said animation attribute.

13. The method of claim 11 wherein animating each of said graphical objects on said screen display in relation to associated user biometric data comprises varying over a period of time said attribute of each of said graphical objects.

14. The method of claim 13 wherein said attribute of said graphical object is selected from the group consisting of:

speed, size, color, color saturation, and height on the screen.

15. The method of claim 13 wherein said time period is a day.

16. The method of claim 13 wherein said time period is a period of minutes.

17. The method of claim 13 wherein said attribute intensifies when new biometric data is received.

18. The method of claim 13 wherein said attribute of said graphical object is a location of said graphical object on said screen display.

19. The method of claim 11 wherein said user biometric data is received from a heart rate sensor.

20. The method of claim 19 wherein said heart rate sensor is selected from the group consisting of:

hand grip sensors, ear clip sensors, and finger sensors.

\* \* \* \* \*